US009333075B2

(12) United States Patent
Biadillah et al.

(10) Patent No.: US 9,333,075 B2
(45) Date of Patent: May 10, 2016

(54) VALVE REPLACEMENT DEVICES, DELIVERY DEVICE FOR A VALVE REPLACEMENT DEVICE AND METHOD OF PRODUCTION OF A VALVE REPLACEMENT DEVICE

(75) Inventors: Youssef Biadillah, Lausanne (CH); Stephane Delaloye, Bulach (CH); Fabien Lombardi, Prilly (CH); Jean-Luc Hefti, Cheseaux-Noreaz (CH)

(73) Assignee: Symetis SA, Ecublens VD (CH)

( * ) Notice: Subject to any disclaimer, the term of this patent is extended or adjusted under 35 U.S.C. 154(b) by 83 days.

(21) Appl. No.: 13/821,476

(22) PCT Filed: Sep. 12, 2011

(86) PCT No.: PCT/EP2011/065744
§ 371 (c)(1),
(2), (4) Date: Oct. 3, 2013

(87) PCT Pub. No.: WO2012/032187
PCT Pub. Date: Mar. 15, 2012

(65) Prior Publication Data
US 2014/0018915 A1   Jan. 16, 2014

(30) Foreign Application Priority Data

Sep. 10, 2010 (EP) .................................... 10176281
Jan. 11, 2011 (EP) .................................... 11150544
May 15, 2011 (EP) .................................... 11004013
May 16, 2011 (EP) .................................... 11166201

(51) Int. Cl.
*A61F 2/24* (2006.01)
*A61F 2/95* (2013.01)

(52) U.S. Cl.
CPC ....... *A61F 2/2418* (2013.01); *A61F 2002/9505* (2013.01); *A61F 2220/0075* (2013.01); *A61F 2230/0013* (2013.01)

(58) Field of Classification Search
CPC ............................. A61F 2/2412; A61F 2/2418
USPC ................... 623/1.23, 1.24, 1.26, 2.11–2.15, 623/2.17–2.19
See application file for complete search history.

(56) References Cited

U.S. PATENT DOCUMENTS 5,163,955 A   11/1992   Love et al.
5,571,174 A   11/1996   Love et al.
(Continued)

FOREIGN PATENT DOCUMENTS

DE   202010007592 U1   10/2010
EP         2033593 A1    3/2009
(Continued)

OTHER PUBLICATIONS

International Search Report for International Application No. PCT/EP2011/065744, date of mailing Feb. 17, 2012.

*Primary Examiner* — Thomas J Sweet
*Assistant Examiner* — Daniel Bissing
(74) *Attorney, Agent, or Firm* — Cooley LLP

(57) ABSTRACT

A device for heart valve replacement comprises a valve component having at least two valve leaflets preferably made of pericardium tissue. Each valve leaflet includes at least two tabs. The device further includes a stent component configured to be radially compressible into a compressed state and expandable into a functional state. The stent component comprises a first end, a second end and at least one intermediate section arranged between said first and said second end. The intermediate section has at least two commissural posts generally aligned parallel to an axis spanning from the first end to the second end. The commissural posts are formed in the shape of a wishbone.

20 Claims, 5 Drawing Sheets

(56) References Cited

U.S. PATENT DOCUMENTS

Figure 1:
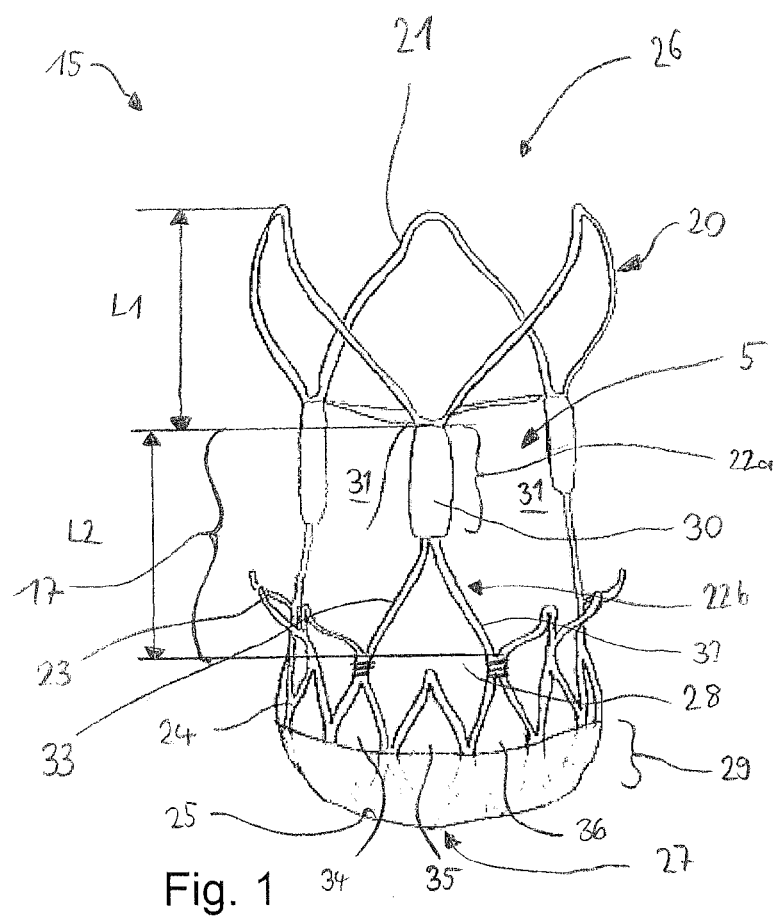

| | | |
|---|---|---|
| 5,653,749 A | 8/1997 | Love et al. |
| 5,807,241 A | 9/1998 | Heimberger |
| 5,989,280 A | 11/1999 | Euteneuer et al. |
| 7,329,278 B2 | 2/2008 | Seguin et al. |
| 2002/0032481 A1 | 3/2002 | Gabbay |
| 2002/0177894 A1 | 11/2002 | Acosta |
| 2003/0212447 A1 | 11/2003 | Euteneuer et al. |
| 2004/0260389 A1* | 12/2004 | Case et al. ............ 623/1.24 |
| 2005/0113910 A1 | 5/2005 | Paniagua et al. |
| 2005/0182483 A1 | 8/2005 | Osborne |
| 2006/0025844 A1 | 2/2006 | Majercak et al. |
| 2006/0259136 A1* | 11/2006 | Nguyen et al. ............ 623/2.18 |
| 2006/0259137 A1* | 11/2006 | Artof et al. ............ 623/2.18 |
| 2006/0282157 A1* | 12/2006 | Hill et al. ............ 623/1.24 |
| 2007/0233222 A1 | 10/2007 | Roeder et al. |
| 2008/0071361 A1 | 3/2008 | Tuval et al. |
| 2009/0099554 A1 | 4/2009 | Forster et al. |
| 2010/0082094 A1* | 4/2010 | Quadri et al. ............ 623/1.26 |
| 2010/0100167 A1 | 4/2010 | Bortlein et al. |
| 2010/0168834 A1 | 7/2010 | Ryan et al. |
| 2010/0185277 A1* | 7/2010 | Braido et al. ............ 623/2.18 |
| 2011/0295363 A1* | 12/2011 | Girard et al. ............ 623/1.26 |
| 2013/0274870 A1 | 10/2013 | Lombardi et al. |
| 2014/0200649 A1 | 7/2014 | Essinger et al. |

FOREIGN PATENT DOCUMENTS

| | | |
|---|---|---|
| EP | 2474287 A1 | 7/2012 |
| JP | 2010-528761 A | 8/2010 |
| WO | 9415549 A1 | 7/1994 |
| WO | 0205885 A2 | 1/2002 |
| WO | 2007005799 A1 | 1/2007 |
| WO | WO 2007/071436 | 6/2007 |
| WO | 2008150529 | 12/2008 |
| WO | 2009002548 A1 | 12/2008 |
| WO | WO 2009/053497 | 4/2009 |
| WO | WO 2009053497 A1 * | 4/2009 |
| WO | 2009091509 A1 | 7/2009 |
| WO | 2009149462 A2 | 12/2009 |
| WO | 2010045297 A2 | 4/2010 |
| WO | 2011051043 A1 | 5/2011 |
| WO | 2012032187 A1 | 3/2012 |
| WO | 2012038550 A1 | 3/2012 |
| WO | 2012/095455 A2 | 7/2012 |

\* cited by examiner

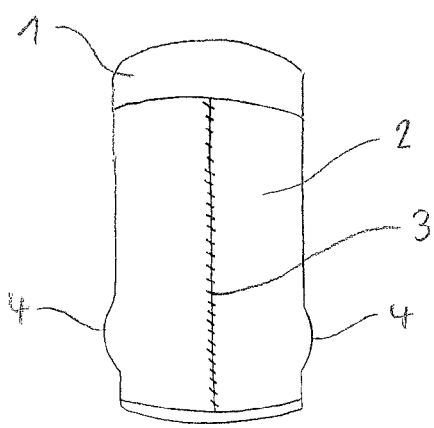 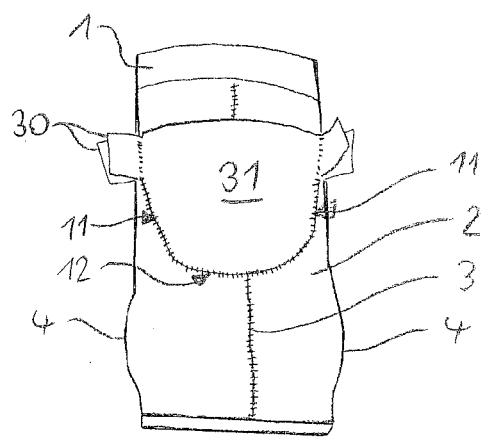
Fig. 5a  Fig. 5b
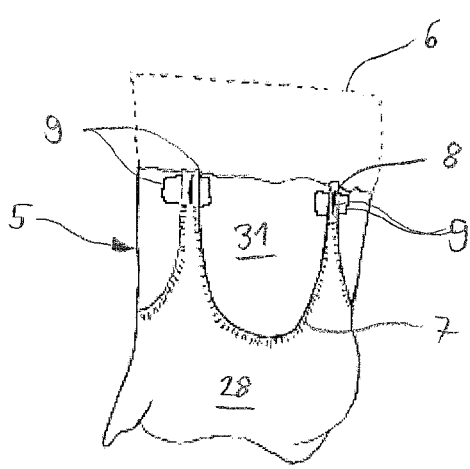 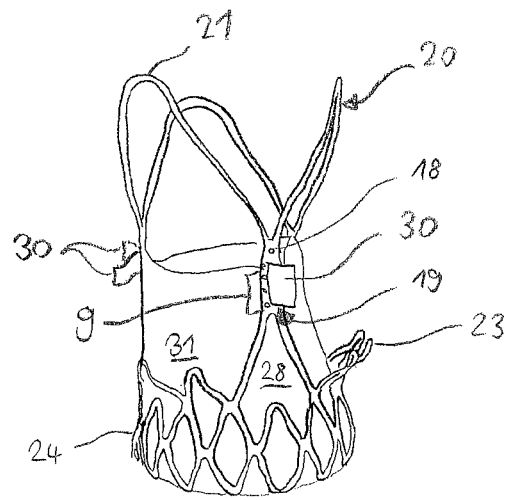
Fig. 5c  Fig. 5d
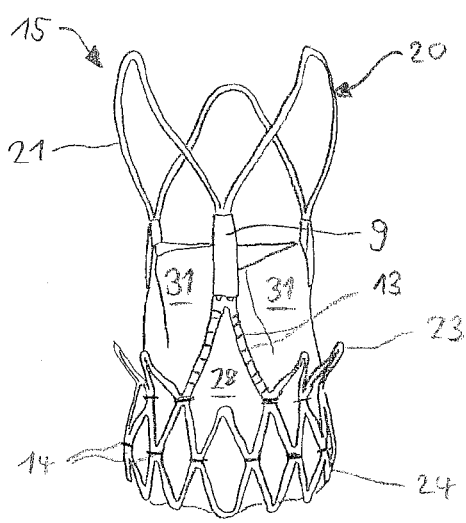
Fig. 5e

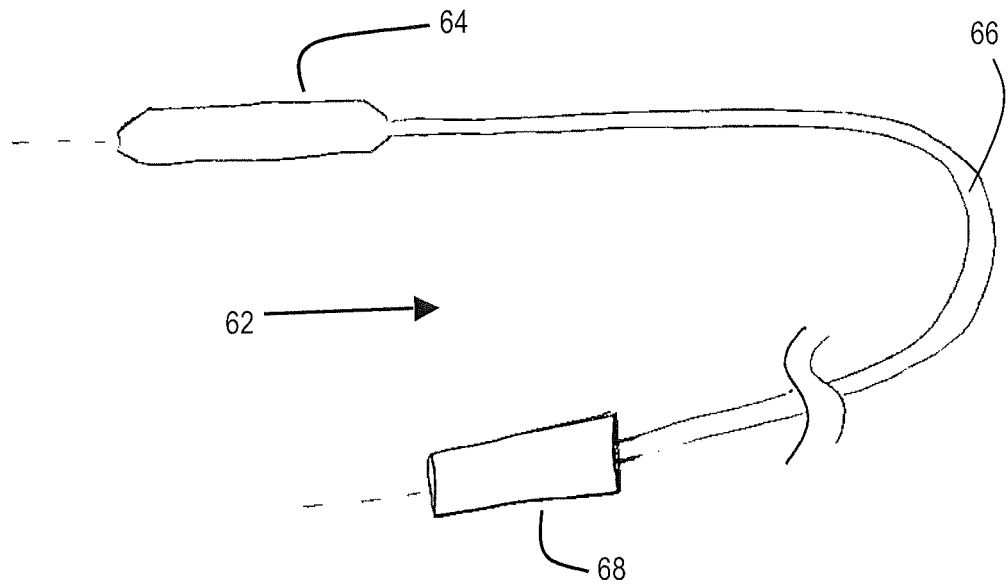
FIG. 7
FIG. 8
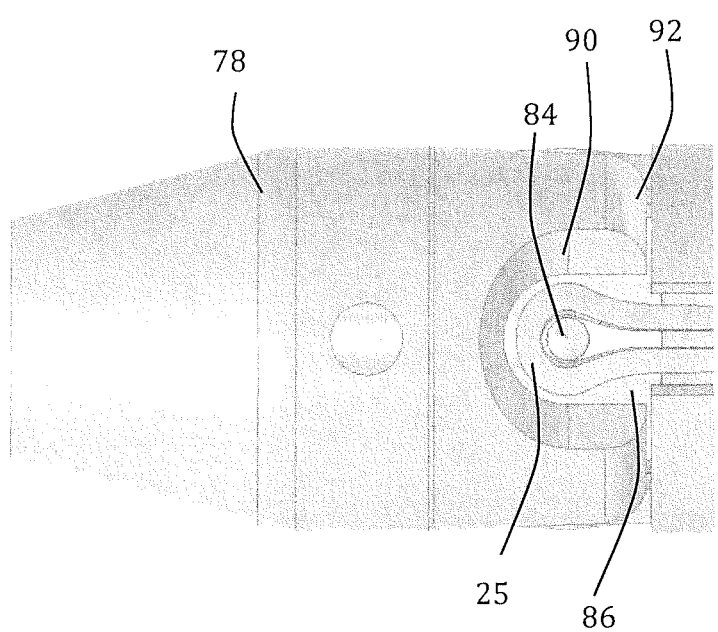
FIG. 9
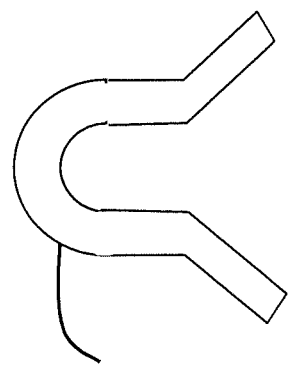

VALVE REPLACEMENT DEVICES, DELIVERY DEVICE FOR A VALVE REPLACEMENT DEVICE AND METHOD OF PRODUCTION OF A VALVE REPLACEMENT DEVICE

CROSS-REFERENCE TO RELATED APPLICATIONS

The present application is a 35 U.S.C. §371 national stage entry of PCT/EP2011/065744, which has an international filing date of Sep. 12, 2011 which claims priority to European Patent Application Nos. 10176281.3, filed Sep. 10, 2010; 11150544.2 filed Jan. 11, 2011; 11004013.6 filed May 15, 2011 and 11166201.1 filed May 16, 2011, the disclosures of which are incorporated herein by reference in their entireties.

The present invention is directed to devices for valve replacement, especially of the aortic valve. Further, the present invention is also related to a delivery device for a valve replacement device and to a method of production of a valve replacement device. Valve replacement devices may also be referred to a stent-valves or valved-stents.

Conventional approaches for cardiac valve replacement require the cutting of a relatively large opening in the patient's sternum ("sternotomy") or thoracic cavity ("thoracotomy") in order to allow the surgeon to access the patient's heart. Additionally, these approaches require arrest of the patient's heart and a cardiopulmonary bypass (i.e., use of a heart-lung bypass machine to oxygenate and circulate the patient's blood). In recent years, efforts have been made to establish a less invasive cardiac valve replacement procedure, by delivering and implanting a cardiac replacement valve via a catheter inserted through a smaller skin incision via either a transvascular approach—delivering the new valve through the femoral artery, or by transapical route, where the replacement valve is delivered between ribs and directly through the wall of the heart to the implantation site.

Stent valves and delivery systems for placing a replacement valve via a catheter are known in the art, and are disclosed for example in WO 2007/071436 and WO 2009/053497.

Some known stents are made from a shape memory material, such as Nitinol, and are self-expanding. The valves may be from animals, for example porcine aortic valves. Alternatively the valves may at least partly be made of synthetic material, such as Dacron.

For example, the WO 2007/071436 discloses a valve replacement device comprising a valve element and a stent element. The stent element includes three different sections, wherein one section houses the valve element. The valve element includes three leaflets, which may be made of biological or artificial material. The three different sections may be provided with different diameters.

One major drawback of some known replacement valve stents is that even in a collapsed (crimped) state their diameter is often too big for transvascular delivery of the stent. Transfemoral delivery of the stent, where the stent has to be advanced over the aortic arch, requires even smaller diameters of less than 18 French (6 mm). Such small diameters may also be useful in transapical delivery if a smaller skin incision and/or smaller cut in the heart wall may be used.

Crimping some known stent valves to a diameter of less than 18 French would produce high strains on the replacement valve, which may lead to damages.

Thus there is a need for replacement valve devices, which avoid the disadvantages of the known and which in particular may be crimped to small diameters without the risk of damaging the replacement valves and which may be reliably placed and tightly anchored over an aortic annulus.

Aspects of the invention are defined in the claims.

Broadly speaking, one aspect of the invention provides a device for heart valve replacement, comprising a valve component (and/or a tissue valve) with at least two valve leaflets. The term "valve component" is used herein to refer to the leaflets collectively, whether or not the leaflets are secured together to define a unitary valve structure independent of other components.

The leaflets are preferably made of pericardium tissue, most preferably from porcine pericardium tissue or bovine pericardium. Porcine pericardium may be desirably thin and sufficiently durable. Bovine pericardium may be thicker and even more durable when this is desired. Each valve leaflet includes at least two tabs. The device further includes a stent component configured to be radially compressible into a compressed state and expandable into a functional state. The stent component comprises a first end, a second end and at least one intermediate section arranged between said first and said second end. The intermediate section has at least two commissural posts optionally and/or generally aligned parallel to an axis spanning from the first end to the second end. The tabs of the leaflets are directly attached to the commissural posts, preferably to attachment means provided on said commissural posts.

The valve leaflets are configured and dimensioned such as to form a replacement valve. In some embodiments, the leaflets have a straight or slightly curved upper free edge, two lateral edges and a substantially arcuate lower edge. At least one tab is arranged on each lateral edge, preferably in the area of the upper free edge of the leaflet. In the valve replacement device, the at least two leaflets are positioned such that their upper free edges may be pressed together to prevent blood flow in one direction, e.g. towards the heart during diastole in the case of an aortic valve replacement, and move apart to allow blood flow in the other direction, e.g. away of the heart during systole.

More preferably, three valve leaflets are provided. This allows to mimic the natural tricuspid valve architecture e.g. of the aortic, pulmonary, tricuspid or mitral valve. Alternatively, the valve replacement device may also comprise more leaflets, such as four, five or more.

While it is known to use a large selection of different artificial materials for replacement valves, it is preferred that the at least two leaflets of the valve replacement device according to the present invention are made of pericardium tissue. Most preferably, the at least two leaflets are made from porcine pericardium tissue. Pericardium tissue is sufficiently thin and yet durable enough to be used as leaflet material. The porcine heart shows a lot of similarities to the human heart. Therefore it is advantageous to use porcine pericardium tissue. Further, porcine pericardium tissue is readily available. For the present invention, the use of a porcine aortic valve is not indicated, since it is too thick and would not allow the crimping of the valve replacement device to less than 20 French. As mentioned previously, bovine pericardium may also be used for the leaflets where even greater durability is desired, optionally at the expense of thicker tissue.

The stent component preferably is of the self-expanding type. Such stents are known in the art and often comprise or are made of a shape-memory material, such a Nitinol. Alternatively, the stent component may be made of or comprise a plastically deformable material and may be expanded to the functional state by external means, such as a balloon catheter.

In the compressed, e.g., the crimped state, the stent component may be inserted in the area of a heart valve of a patient, such as the aortic valve. Further, the diameter of the stent component in the compressed state is such that it may be advanced into a patient's heart through an artery, such as the femoral artery. The diameter and/or the flexibility of the stent component in the compressed state are therefore preferably such that the valve replacement device may be advanced through the aortic arch.

In the functional state, the stent component is in an at least partly expanded, or non-compressed configuration. Optionally, the stent component defines an interior conduit space. The conduit space may be generally cylindrical and/or tubular. The valve leaflets are arranged to span the interior space within the stent component. Once the valve replacement device is positioned at a target position close to the natural valve of a patient, the stent component is expanded to its functional state. Preferably the stent component may additionally comprise anchoring elements which allow a secure attachment of the device within a cardiovascular vessel upon expansion of the stent element.

The natural valve leaflets of the patient may be pushed aside by the expanding stent component. Once fully expanded, the valve component arranged within the stent component will take over the function of the natural valve.

The stent component preferably comprises a first end, a second end and at least one intermediate section arranged between said first and said second end. The valve component is thereby preferably arranged within said intermediate section of the stent component. Optionally, the stent component is configured such that said intermediate section includes a conical and/or cylindrical conduit space, optionally with a constant diameter, said diameter most preferably being in the range of 15 mm to 35 mm. The length of said intermediate section thereby preferably is in the range of 10 mm to 50 mm.

In the functional state, said first and said second ends define inflow and outflow openings through or around which blood may flow in use. A simple embodiment of a valve replacement device according to the present invention may comprise only the intermediate section including a first and a second end. However, more preferably a valve replacement device according to the present invention comprises at least an additional inflow and/or an additional outflow section arranged between said intermediate section and said first and/or said second end.

"Inflow section" as understood herein is the section of the stent component where blood enters into said conduit space and/or the section of the stent component that, in use, is upstream of the valve leaflets; for example, in the case of a semilunar and/or aortic valve, the section of the stent component which is oriented towards the ventricle.

Accordingly, an "outflow section" as understood herein is the section of the stent component where blood leaves said conduit space and/or the section of the stent component that, in use, is downstream of the valve leaflets; for example, the section which is located in the artery for semilunar valves.

Said inflow and said outflow section may thereby have the same length or have different lengths. Further, said inflow and/or said outflow section may define a generally tubular conduit interior conduit space. The conduit space may be generally cylindrical. More preferably, said inflow and/or said outflow section include a generally conical conduit, i.e. a conduit with an increasing or a decreasing diameter. Alternatively, the inflow and the outflow section may include an interior conduit space of any appropriate geometric shape.

Optionally, said inflow and said outflow section may have the same maximal diameter or varying maximal diameters. A "maximal diameter" as understood herein is the largest diameter within such a section. Optionally, said inflow section has a smaller maximal diameter than said outflow section. Further, said intermediate section has a diameter which is smaller than the maximal diameter of either of said inflow or said outflow section. Most preferably said inflow and said outflow sections have a diameter which increases in the direction of said first and said second end. Alternatively, further sections may be arranged between said inflow and/or said outflow section and said intermediate section.

In a preferred embodiment, the inflow section has a maximal diameter in the range from 20 mm to 35 mm and the outflow section has a maximal diameter in the range from 20 mm to 55 mm.

The stent component may further comprise a lower anchoring crown. The lower anchoring crown may define an at least partly conical body. Said lower anchoring crown preferably is located between the second end and the intermediate section of the stent component and preferably configured as to be placed within the annulus and/or extend to the ventrical side of the annulus.

Additionally, the stent component may further comprise an upper anchoring crown in communication with or adjacent to the lower anchoring crown. The upper anchoring crown may define an at least partly conical body. Said conical body of said lower anchoring crown may slope outwardly in the direction of the second end and the conical body of the upper anchoring crown may slope outwardly in the direction of the intermediate section, e.g. such as to be placed on the aortic side of the annulus.

Preferably, the stent component further includes stabilization arches which are in communication with the commissural posts and extend towards the first end. The stabilization arches are preferably configured to engage the ascending aorta to orient the stent component longitudinally within the aorta or the aortic annulus, thus tending to correct any tilting of the stent component, with respect to the ascending aorta, during implantation. The commissural posts are thereby connected to each other through the stabilization arches, whereby two adjacent commissural posts are in connection with each other by means of one stabilization arch. Further, the commissural posts preferably are also in communication with the upper anchoring crown and/or the lower anchoring crown.

Further, the stent component preferably comprises at least one attachment element for mating engagement with a delivery device (for example, a stent holder of the delivery device). The at least one attachment element may be configured for restraining axial displacement of the stent component until the stent component is fully released. In some embodiments, the at least one attachment is provided at the lower crown, such that the ventrical part and/or inflow section of the valve replacement device is the last part to expand during placement of the device. The stent component may comprise any suitable number of attachment elements, for example, two, three, or more. The attachment elements may be spaced substantially uniformly in the circumferential direction.

Optionally, the at least one attachment element may comprise a U-shape portion joining two stent struts. The term U-shape is used herein to include any shape including a generally arcuate apex, whether or not the sides are straight or curved, bulged outwardly, parallel or non-parallel. In a collapsed (e.g. compressed) state of the stent when received within the accommodation region of the delivery catheter, the struts may lie adjacent each other at the attachment element, such that the arc of the U-shape portion extends around a first angle more than 180 degrees to define, for example, a closed or near closed (e.g. horseshoe shape) eyelet having an aperture larger than the spacing of the struts. The horseshoe shape of the eyelet aperture and the adjacent space between the struts may together define a keyhole type shape. In an expanded (or non-collapsed) state of the stent when released from the accommodation region of the delivery catheter, the struts may move apart, and the arc of the U-shape portion may extend around a second angle that is less than the first angle, to at least partly open the eyelet further. For example, the second angle may be about 180 degrees or less. In the expanded state, the attached element may define a substantially straight-sided U-shape with an arcuate apex.

The delivery catheter may comprise a sent-holder provided within a stent accommodation region. The stent-holder may comprise
(i) a respective projection receivable within each eyelet. The projection may be dimensioned such that, when the stent component is in its collapsed state, the projection is trapped within the eyelet and unable to pass between the adjacent struts, and/or
(ii) one or more recesses or interstices for accommodating the attachment element substantially therewithin, at least in the collapsed state of the stent component.

The above forms can provide for a compact, yet reliable and self-opening and/or self-releasing attachment between a stent-valve and a delivery system. The provision of the attachment elements also does not impede compressing of the stent component to a desirably small size.

In some embodiments, the intermediate section comprises at least two commissural posts generally aligned parallel to an axis spanning from the first end to the second end. The tabs of the leaflets are directly attached to said commissural posts, preferably to attachment means provided on said commissural posts.

The direct attachment of said leaflets to said commissural posts provides a high strain resistance of the leaflets. Optionally, in comparison to valve replacement stents as known in the art, the direct attachment of the leaflets to the commissural posts may optionally reduce the thickness of the crimped stent element, if excess layers of tissue between the leaflets and the commissural posts capable of withstanding the strain resistance may be avoided.

According to another aspect of the present invention, a device for heart valve replacement is provided which comprises a valve component and/or tissue valve having at least two valve leaflets. Said at least two valve leaflets are preferably made of pericardium tissue, most preferably porcine pericardium tissue. Each of said at least two valve leaflets includes at least two tabs. The device further includes a stent component configured to be radially compressible into a compressed state and expandable into a functional state. The stent component comprises a first end, a second end and at least one intermediate section arranged between said first and said second end. The intermediate section has at least two commissural posts generally aligned parallel to an axis spanning from the first end to the second end. Said commissural posts are formed in the shape of a wishbone and said tabs are directly attached to said commissural posts, preferably to attachment means provided on said commissural posts.

A wishbone is generally shaped like an inverted letter "Y". The commissural posts therefore include two inclined legs (also referred to sometimes as arms) and one stem. The inclined legs may be straight, but preferably the two inclined legs are curved (e.g. around the axis of the stent component and/or in a circumferential plane). The shape, whether straight or curved, is preferably selected such that the legs of the wishbone are substantially in register and/or congruent with the lateral edges of the valve leaflets. This allows the commissural post to provide good support to the lateral edges of the valve leaflets. The lateral edges of the valve leaflets may be attached to the legs, and/or to inner skirt material between the leaflets and the commissural posts. The legs are thereby shaped such as to match generally the contour of the lateral edges of the leaflets. This allows the attachment of the lateral edges of the leaflets directly or indirectly to the legs of the wishbone shaped commissural posts, e.g. by means of a suture, for close support of the leaflets.

The configuration of other elements of this embodiment of a stent valve replacement device is similar to the ones described for the first embodiment above.

The commissural posts preferably comprise attachment means for the tabs of the valve leaflets, said attachment means including at least one opening adapted for the insertion of at least one tab.

Said openings are preferably configured as through holes, i.e. the openings are bounded and/or flanked on all sides by the commissural posts. Alternatively, said openings may also be configured as channel slits, i.e. bounded and/or flanked by the commissural posts only on three sides, while one side is open. The openings may be in any suitably form, like rectangular, round, oval, etc. Most preferably the openings are in the form of a long-hole. The openings are further adapted such that at least one tab of said valve leaflets may be inserted therethrough. Therefore the position of the openings on the commissural posts as well as their size is selected such that at least one tab of a valve leaflet may be inserted. Preferably said openings are adapted such that two tabs, e.g. from two neighbouring valve leaflets, may be inserted. Alternatively, the commissural posts may include more than one such openings. In this way, attachment of valve leaflets having more tabs, such as two tabs on each lateral edge, may be attached to said commissural posts. In a further alternative, the commissural posts may include two openings arranged parallel to each other, such that tabs of neighbouring valve leaflets may each be inserted into a separate opening. The tabs are preferably inserted into an opening, folded back over the commissural post towards the valve leaflet and sutured thereto.

Said attachment means may additionally include at least two bores adapted for the insertion of a suture wire, said bores preferably being in the form of round-bores. Provision of such additional bores facilitates the attachment of said tabs and/or of the lateral edges of the leaflets to said commissural posts.

These additional at least two bores are preferably provided flanking said at least one opening.

The stent component preferably comprises a substantially parallel and/or non-parallel tubular portion arranged between said intermediate section and said second end, said tubular portion having a lattice structure of at least one row of cells, the wishbone shape of each commissural post spanning a respective sequence of at least three adjacent cells, such that the wishbone extends from outer cells of the sequence without attachment to the at least one intermediate cell of the sequence. Such an arrangement provides for ease of compression, while allowing the wishbone legs to have sufficient divergence to match the shape of the lateral edges of the leaflets.

In some embodiments, the legs of the wishbone are joined to the outer cells of the sequence in the lattice structure, therefore allowing the commissural post to span over at least three adjacent cells without being attached to the at least one intermediate cell. Alternatively, each commissural post may be configured to span over more than three adjacent cells, such as four, five, etc. Further alternatively, each commissural post may be configured to span a different number of adjacent cells. Preferably, the stems of the wishbone shaped commissural posts are in communication with each other by means of stabilization arches. The stems of two adjacent wishbone shaped commissural posts are thereby in communication with each other by means of one stabilization arch.

The valve replacement device additionally may comprise an inner skirt, preferably made of pericardium tissue, and attached to the leaflets. The inner skirt may serve to channel blood within the conduit space of the stent component, and obstruct leakage of blood through interstices of the stent component (e.g. through cells of a lattice structure).

In some embodiments, the inner skirt may have commissural portions spaced apart by scalloped clearances (e.g. scalloped cutouts). Each clearance is spanned by a respective valve leaflet. The lateral edges and/or lower edges of the leaflets may be attached to the inner skirt, for example, by sutures.

In some embodiments, the inner skirt may extend towards said second end, said skirt preferably being sutured to said stent device. Said skirt preferably covers at least partly an interior surface of the stent component. This reduces the occurrence of turbulent flow of the blood which may be triggered by the material of the stent component. Said skirt preferably is further sutured to said at least two valve leaflets.

Additionally, at least one section of said stent component is at least partially covered on the outside by an outer skirt.

The stent component is preferably configured such that when the valve replacement device in the compressed state is inserted into the sheath of a delivery device, such as a catheter, the aggregated diameter of the delivery device and the sheath is less than 20 French, preferably less than 18 French. This allows the insertion of the valve replacement device along an artery, preferably the femoral artery or the subclavian artery. It may also enable the valve replacement device to be inserted transapically using a small skin incision and/or cut through the heart wall.

According to yet another aspect of the invention there is provided a device for heart valve replacement comprising a valve component and/or tissue valve, including at least two valve leaflets each having at least two tabs. The at least two leaflets may be attached to an annular skirt on the inside of the skirt. The term "annular" as used herein is meant to designate a circumferentially running structure and is not limited to an exactly circular or ring like structure. A portion of the skirt material wraps at least partially around the commissural post without passing through the tab opening.

According to still another aspect of the invention there is provided a device for heart valve replacement comprising a stent component having at least one section defining an at least partially conical body. The device further has a plurality of valve leaflets. An inner skirt is disposed within the stent component overlapping said at least partially conical body to define a conduit therewithin. An outer skirt is disposed outside the stent component overlapping only a portion of said at least partially conical body.

The inner skirt and/or the outer skirt are preferably made of pericardium tissue, most preferably porcine pericardium tissue.

Another aspect of the invention provides a valve replacement device comprising a stent component that is radially compressible to a compressed state for delivery and radially expandable to a functional state. The stent component may comprise at least one (and preferably a plurality) of attachment elements for cooperating with a stent-holder of a delivery device. Each attachment element (or at least one of the attachment elements) may comprise a U-shape portion joining two stent struts. The term U-shape is used herein to include any shape including a generally arcuate apex, whether or not the sides are straight or curved, bulged outwardly, parallel or non-parallel. In the compressed state of the stent when received within an accommodation region of the delivery catheter, the struts may lie adjacent each other at the attachment element, such that the arc of the U-shape portion extends around a first angle more than 180 degrees to define, for example, a closed or near closed (e.g. horseshoe shape) eyelet having an aperture larger than the spacing of the struts. The horseshoe shape of the eyelet aperture and the adjacent space between the struts may optionally together define a keyhole type shape. In an expanded (or non-collapsed) state of the stent when released from the accommodation region of the delivery catheter, the struts may move apart, and the arc of the U-shape portion may extend around a second angle that is less than the first angle, to at least partly open the eyelet further. For example, the second angle may be about 180 degrees or less. In the expanded state, the attached element may define a substantially non-horseshoe U-shape, for example, a straight-sided U-shape with an arcuate apex.

A delivery device for use with a valve replacement device as aforesaid may comprise a sent-holder provided within an accommodation region. The stent-holder may comprise (i) a projections receivable within each eyelet. The projection may be dimensioned such that, when the stent is in its collapsed state, the projection is trapped within the eyelet and unable to pass between the adjacent struts, and/or (ii) one or more recesses or interstices for accommodating the attachment element substantially therewithin, at least in the collapsed state of the stent.

The above forms can provide for a compact, yet reliable and self-opening and/or self-releasing attachment between a valve replacement device and a delivery device.

Another aspect of the present invention provides a valve replacement device comprising a stent component supporting at least two leaflets. The leaflets may be of pericardium tissue, most preferably porcine pericardium tissue or bovine pericardium. As mentioned previously, porcine pericardium may provide desirable tissue thinness. Bovine pericardium may be slightly thicker but more durable.

Each valve leaflet may include at least two tabs. The tabs may serve for supporting the leaflets relative to the stent component.

In some embodiments, the tabs may be attached directly to commissural supports (e.g. posts) of the stent component. The tabs may attach to attachment means provided on the commissural support. For example, a tab may pass through an opening (e.g. a slot or slit) in a commissural support, from an interior of the stent component to an exterior. The portion of the tab exterior to the stent component may be folded to lie against the commissural support and/or sutured to the commissural support. Optionally respective tabs of two adjacent leaflets that meet at the commissural support pass through the same opening. Each tab may be folded to lie against the exterior of the commissural support without overlapping the other tab. The two tabs optionally are not directly attached to each other.

Additionally or alternatively, the leaflets may be attached to an inner skirt. The leaflets may be attached to an interior portion of the inner skirt, the tabs passing through openings (e.g., slots or slits) in the inner skirt to the exterior of the inner skirt. The inner skirt may have scalloped clearances, each such clearance being spanned by a respective leaflet. The inner skirt may have commissural portions or upstands in which the openings (e.g., slots or slits) are provided.

Additionally or alternatively, the material defining the inner skirt may include integral extension portions (e.g. flaps) that wrap around at least a portion of the commissural supports, for covering portions of the commissural supports and/ or for covering the leaflet tabs secured to the commissural supports. The extension portions may be sutured to the commissural supports.

In some embodiments, a combination of any two or all three of the above arrangements may be used. For example, a pair of tabs of adjacent leaflets may pass through an opening in the inner skirt, and through an opening in the commissural support. The two openings may generally be in register. The tabs may be folded back in opposite directions, and sutured to the exterior of the commissural support (optionally without the tabs being sutured directly to each other). One or more flaps or extensions of the inner skirt at the commissural support may be wrapped around the exterior of the commissural support to cover the tabs and/or the commissural support. The extension(s) may be sutured to the commissural support. Optionally, the sutures may pass through the same suture holes in the commissural support as those used for attaching the tabs. The extension(s) may extend axially beyond the tab(s), such that the edges of the tabs are shrouded and protected.

Another aspect of the invention provides a valve replacement device comprising a stent component that is radially compressible to a compressed state for delivery and radially expandable to a functional state, a plurality of valve leaflets mounted within the stent component, an inner skirt attached to the valve leaflets, the inner skirt extending at least partly within the stent component, and an outer skirt extending at least partly outside the stent component.

In some embodiments, the outer skirt may extend further towards an inflow extremity of the stent component than does the inner skirt. Additionally or alternatively, the inner and outer skirts may partly overlap, at least with respect to the surface of at least one of the skirts. Additionally or alternatively, the inner and outer skirts may not have any coterminous extremity. Additionally or alternatively, the inner skirt may extend further towards an outflow extremity of the stent component than does the outer skirt.

At least a portion of the stent component over which at least one of the skirts extends, may optionally comprise a lattice structure having at least one row of a plurality of cells.

A function of the inner skirt may be to define a conduit within the stent to channel blood towards the valve leaflets, and obstruct leakage of blood through interstices of the stent component (e.g., lattice intertices). A function of the outer skirt may be to provide a seal surface outside the stent component for sealing with surrounding tissue, to obstruct leakage at the interface with surrounding tissue. Providing both skirts may be beneficial in terms of obstructing leakage overall. However, the presence of both skirts can add significantly to the thickness of material carried by the stent, and thereby increase the difficulty of compressing the stent-valve to a desirably small size. By providing both skirts, with only partial overlap in an axial direction, the benefits of both skirts can be obtained, but with a reduced thickness profile in the regions where only one skirt extends. Overlapping the skirts can provide better sealing between the skirts than were the skirts to be arranged edge to edge on the interior and exterior respectively of the stent component (for example, especially bearing in mind that the stent-valve is to be deformed substantially by compression for delivery and re-expansion at implantation).

The degree of skirt overlap in the axial direction may, for example, by at least 1 mm, or at least 2 mm, or at least 3 mm, or at least 4 mm, or at least 5 mm, or at least 6 mm, or at least 7 mm, or at least 8 mm. Additionally or alternatively, the degree of skirt overlap in the axial direction may, for example, be less than 10 mm, or less than 9 mm, or less than 8 mm, or less than 7 mm, or less than 6 mm, or less than 5 mm, or less than 4 mm. For example, the degree of skirt overlap in the axial direction may be about 4-6 mm.

At least one of the skirts (optionally each skirt) may extend a non-overlapped axial distance of at least 1 mm away from the region of overlap. The non-overlapped distance for the or each skirt may, for example, be at least 2 mm, or at least 3 mm, or at least 4 mm or at least 5 mm or at least 6 mm, or at least 7 mm or at least 8 mm or at least 9 mm, or at least 10 mm.

In some embodiments, the inflow edge or mouth of the stent component may have a zig-zag shape defined by a lattice structure of at least one row of cells. The zig-zag shape may be defined an alternating sequence of free apexes (e.g., at or defining an inflow extremity), and connected apexes (e.g. connected to lattice structure extending away from the inflow end towards the outflow end). In some embodiments, the inner skirt may extend only to the connected apexes. The outer skirt may overlap the inner skirt and extend further than the inner skirt, to a level corresponding to at least some of the free apexes.

In some embodiments, the inner skirt may extend towards the inflow extremity of the stent component. The outer skirt may overlap only partly the inner skirt while remaining spaced from an uppermost edge of the inner skirt. The outer skirt may extend towards (or optionally to) the inflow extremity of the stent component. The outer skirt may optionally not overlap (e.g., directly or indirectly through the stent component) any portion of the leaflets.

The inner skirt and/or outer skirt may be of any suitable material, such as pericardial tissue (e.g. porcine pericardium for thinness), PET, Dacron, etc. The inner and outer skirts may optionally be made of the same material as each other.

Another object of the present invention is to provide a delivery system for delivering a device for heart valve replacement. The delivery system comprises a flexible tubular catheter including a proximal end (or portion) and a distal end (or portion) with connection means (e.g. a stent holder). The delivery device further includes a device for heart valve replacement as described hereinabove. The delivery device is connected with said connection means such that the portion of the device adapted to be placed in or towards the ventricle is oriented towards the distal end of said catheter and the portion of said device adapted to be placed in the aorta is oriented toward said proximal end. In connection with the delivery device, the term "distal" means oriented away and the term "proximal" means oriented towards an operator of the delivery device.

The proximal end of the tubular catheter preferably includes a handle member for an operator. The distal end of the tubular catheter comprises connection means (e.g. stent holder) for releasably connecting a valve replacement device according to the present invention. The connection means may be of any suitable type. Preferably, the connection means are configured as pins or other projections that mate with corresponding attachment elements (e.g. hooks and/or eyelets) on the valve replacement device. Upon expansion of the stent component of the replacement device, the attachment elements are released from the pins, thus uncoupling the device from the tubular catheter.

The orientation of the valve replacement device on the tubular catheter allows the insertion of the device along an artery of a patient, preferably along the femoral or the subclavian artery. An arterial insertion is beneficial for some patients, as the procedure is less traumatizing than a surgical procedure. If desired, the tubular catheter may also be configured for transapical insertion.

According to still another aspect of the invention there is provided a method of replacement of a heart valve. A delivery device as disclosed above is inserted in a compressed state to the site of a heart valve to be replaced. The sent element is then expanded. The delivery device is optionally inserted by means of a flexible tubular catheter along an artery, preferably a femoral artery or a subclavian artery. Alternatively the delivery device is inserted transapically into a ventricle of the heart.

It is another objective of the present invention to provide a method of producing a valve replacement device having a reduced size when radially compressed which is quick and easy to perform. This objective is met by a manufacturing method as defined in the appended claims.

In some embodiments, in a first step of the method of production of a valve replacement device according to the present invention, a tubular skirt, preferably made of pericardium tissue, is provided. The term "tubular" has to be understood as to also encompass skirts which are generally shaped like a cylinder or a conical frustum. It also comprises skirts having elliptical cross sections, varying radii along an axis and the like. The tubular skirt preferably is made of porcine pericardium tissue.

In a next step, at least two leaflets, preferably also made of pericardium tissue are arranged adjacent to each other around the tubular skirt. The size of the leaflets is thereby selected such that once the leaflets are each arranged adjacent to each other, they span around the entire circumference of the tubular skirt. The lateral edges of said leaflets are thereby in contact at least in the area of their upper free edge.

The leaflets may be cut out of pericardium tissue. The leaflets include a free edge which is optionally curved. The curvature may be a convex curvature. The size of the leaflets as well as the curvature of the free edge are thereby chosen in such a way as to allow the free edges to sealingly contact each other (e.g. coapt) when the stent component is in the functional state. The leaflets further include two lateral edges tapering towards a lower edge of the leaflet. The lower edge is shorter than the free edge. Preferably, said lower edge is also curved, more preferably with a convex curvature. The term "convex" is understood to define the curvature of an edge of the leaflet in relation to the surface of the leaflet. Therefore, a convexly curved edge bulges out of the leaflet.

Prior to the cutting, the pericardium tissue is preferably treated to avoid any shrinkage of the leaflets at a later stage.

The lateral edges and the bottom edge of the leaflets are then attached onto the surface of the tubular skirt, preferably by means of a suture. Alternatively, the leaflets may also be attached by other means, such as gluing or the like. The free edges must remain unattached to the skirt, as they will form the replacement valve in the assembled valve replacement device.

In the next step, the tubular skirt is everted, so that the leaflets now lie inside the generally tubular conduit of the tubular skirt. The everted skirt is then finally attached to a stent component.

As the valve component of a valve replacement device produced according to the method of the present invention is made "inside out", the attachment of the leaflets to the skirt is much easier and requires lesser steps.

To further reduce the size of the crimped valve replacement device, at least some skirt tissue overlapping the leaflets is preferably removed. This may be done by cutting the skirt along the suture attaching the leaflets to the skirt. The removal of the tissue is preferably performed using scissors or a scalpel. This allows to further reduce the diameter of the valve replacement device, as, with the exception of the area of sutures, only one layer of tissue is present. Removal of such skirt tissue creates scalloped clearances in the skirt tissue, spanned by the leaflets. The skirt tissue may include commissural portions where neighboring leaflets meet. The commissural portions may include circumferential and/or axial extensions (e.g. flaps) for providing protective wrap material for wrapping around the exterior of a commissural post of a stent component.

The at least two leaflets preferably additionally comprise at least two tabs, preferably one tab is thereby arranged on each lateral edge of each leaflet, most preferably in the area of said free edge. Alternatively, the at least two leaflets may comprise more tabs, e.g. two tabs on each lateral edge of each leaflet. After eversion of the tubular skirt, at least two slits are cut into the skirt and at least one tab is inserted through each slit. Alternatively, two tabs of adjacent leaflets are inserted through the same slit. This allows to pass the tabs from the inside of the skirt to the outside.

The tabs are then preferably directly attached to the stent component, preferably to attachment means provided on the stem of a wishbone shaped commissural post, most preferably by pulling said tabs through openings provided on said commissural posts, followed by suturing said tabs to said commissural posts. Superfluous material of said tabs may then be removed.

The extensions of the commissural portions of the skirt material may be wrapped around the commissural posts without passing through the same openings as the tabs.

Preferably, said tubular skirt is made by wrapping a generally rectangular piece of pericardium having an appropriate size around a mandrel having a size and form corresponding to the intended size and form of the valve component of the valve replacement device. The piece of pericardium is then stitched together such as to yield a generally tubular skirt. The pericardium is then preferably treated to cause shrinkage of the tissue, whereby the annular skirt will adopt the form of the outer contour of the mandrel. The mandrel may therefore additionally impart a specific shape to the annular skirt. In a especially preferred embodiment, said mandrel will impart a circumferential bulge on said skirt. During attachment of said at least two leaflets to said annular skirt, the annular skirt may remain on said mandrel.

Further, said flaps of the skirt material may be wrapped over said tabs and said openings, such as to cover the suture holding the tabs on said commissural posts. This further protects the valve replacement device from any damage when crimping the device to less than 18 French in diameter.

While certain aspects of the invention have been defined above and/or in the appended claims, protection is claimed for any novel feature or idea described herein and/or illustrated in the drawings, whether or not emphasis has been placed thereon.

Further advantages and characteristics of the present invention are described in the following description of examples and figures.

Figure 2:
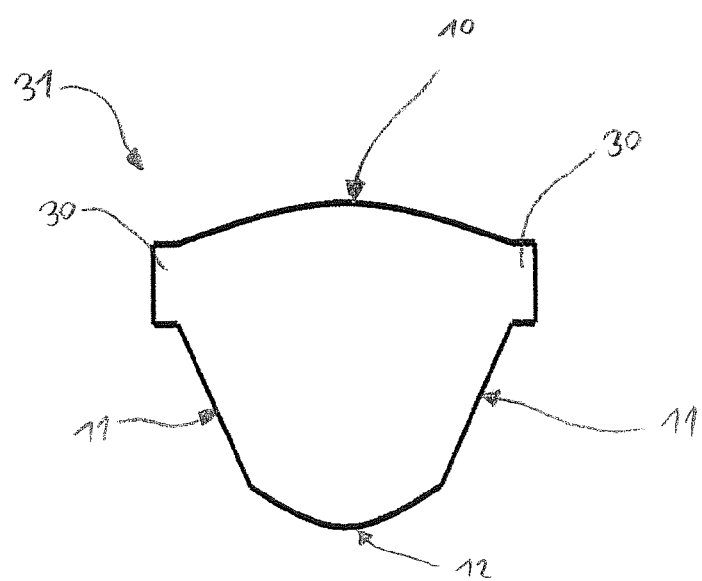
Figure 3:
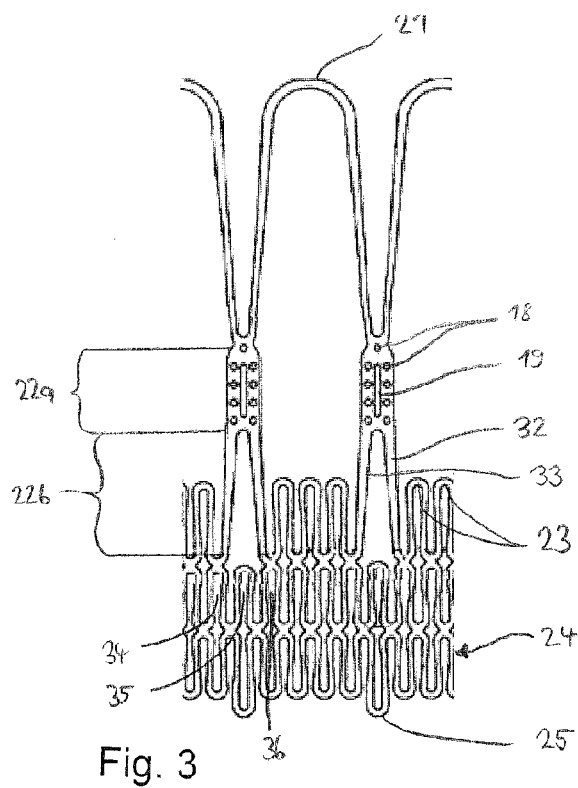
Figure 4A:
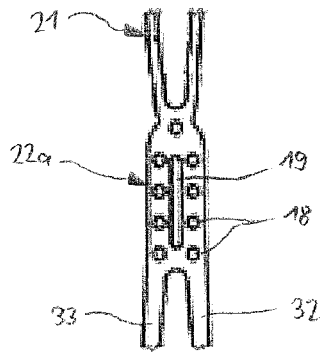
Figure 4B:
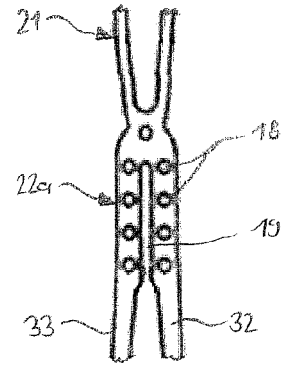
Figure 4C:
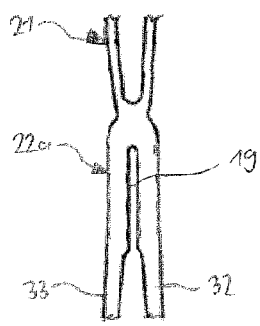
Figure 4D:
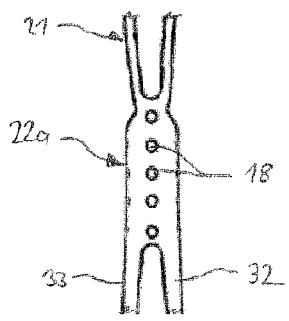
Figure 6:
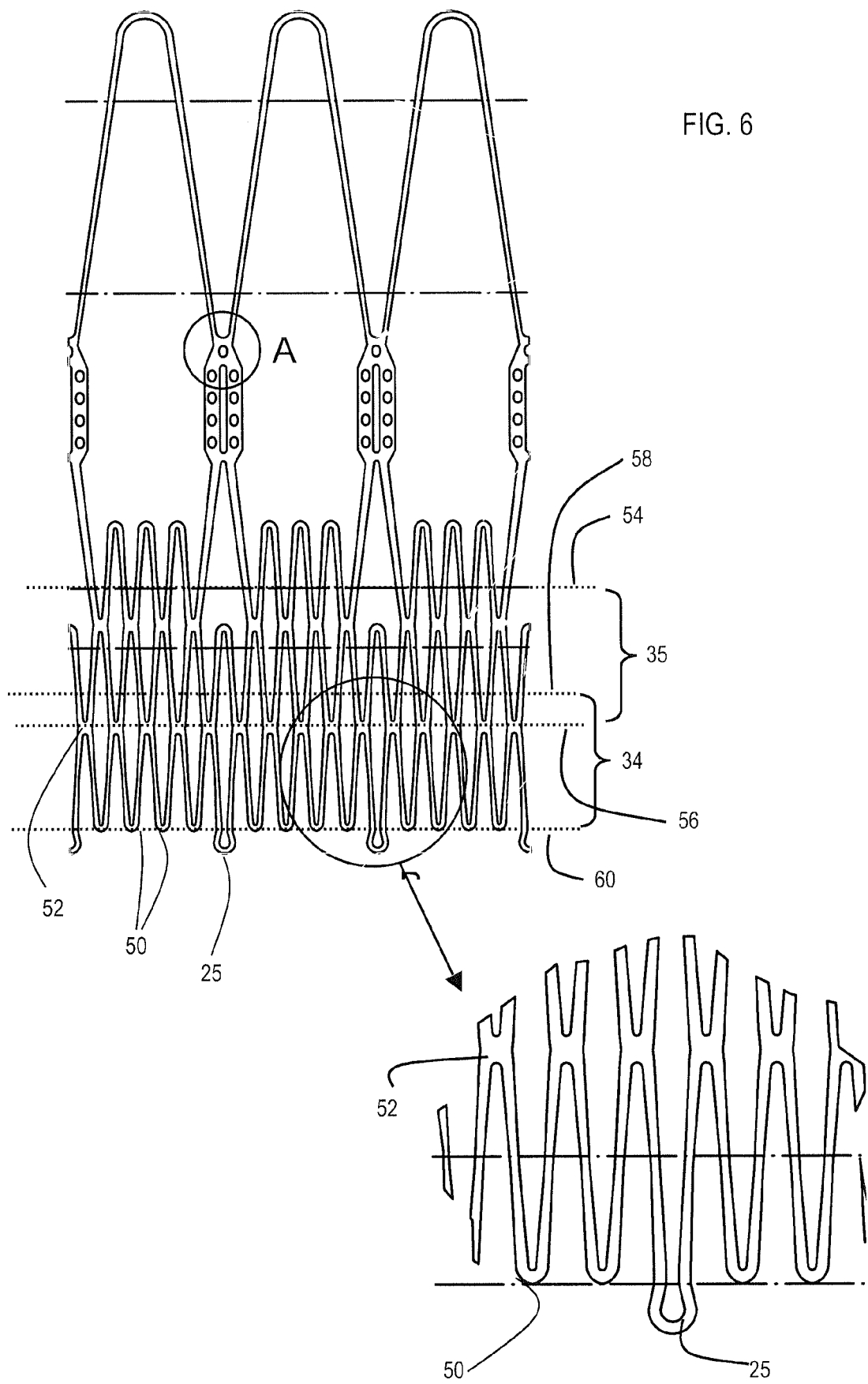

FIG. 1: Shows an exemplary embodiment a valve replacement device according to the present invention;

FIG. 2: shows a leaflet of a valve component according to the present invention;

FIG. 3: shows a detailed view of commissural posts having a wishbone shape;

FIG. 4a-d: are representations of different configurations of attachment means for the tabs of the leaflets;

FIG. 5a-e: shows a method of producing a valve replacement device according to the present invention;

FIG. 6: shows an alternative embodiment of stent component, in a view similar to FIG. 3;

FIG. 7: shows a schematic view of a delivery device for the valve replacement device;

FIG. 8: shows a schematic close-up showing the relation between a stent holder and attachment element when the stent component is in its compressed condition; and FIG. 9: shows schematically the attachment element when the stent component is expanded to its functional state.

FIG. 1 shows a preferred embodiment of a valve replacement device 15 according to the present invention. The valve replacement device 15 is adapted to be inserted by a transfemoral approach, but the device may also be inserted generally by another transvascular approach or by a transapical approach. The replacement device 15 has a first end 26, a second end 27 and an intermediate section 17 and comprises a stent component 20 and a valve component 5. In this embodiment, the first end 26 is intended to be positioned in an artery, while the second end 27 is intended to be positioned in or towards the ventricle of the heart of a patient. When the valve replacement device 15 is in place, blood will flow from the second end 27 to the first end 26 via the intermediate section 17. Therefore, the section between the second end 27 and the intermediate section 17 is also referred to as "inflow section". Accordingly, the section between the intermediate section 17 and the second end 26 is referred to as "outflow section".

The stent component 20 comprises stabilization arches 21, commissural posts 22, upper anchoring crown 23, lower anchoring crown 24 as well as attachment elements 25. The configuration of the stent component is thereby similar to the configuration as described in the co-pending application EP 2 205 183. The stabilization arches 21 serve to stabilize the stent 15 in a blood vessel, preferably the aorta, during deployment. The arches 21 are attached with their proximal end directly to an upper, i.e. distal end of the commissural posts 22. Starting from the proximal end the arches 21 diverge radially outwardly over a part of their length and converge radially inwardly towards their distal end. The terms "distal" and "proximal" are used hereunder to designate the parts of the valve replacement device 15 or of its components lying further away or closer to the heart, respectively. The distal end sometimes is also referred to as the aortic end and the proximal end as the ventricular end.

Three leaflets 31 of a replacement heart valve are attached to the commissural posts 22. The leaflets 31 are formed from porcine pericardium tissue. The upper anchoring crown 23 serves to attach the stent 15 to the aortic side of a heart valve, while the lower anchoring crown 24 serves to attach the stent 15 in the native annulus, or towards the ventricular side of the heart valve. Attachment means 25 enable the removable attachment of the stent 15 to a delivery device.

The commissural posts 22 have an axial length L2 corresponding substantially to the axial length L1 of the stabilization arches 21. Typically the length L1 is about 90% to 110% of the length L2. The commissural posts 22 have a wishbone shape and each include an upper part 22a for direct fixation of tabs 30 of valve leaflets 31 and a lower part 22b with two legs or arms 32, 33. The tabs 30 are fixed to the upper part 22a by wrapping around and suturing. Lateral sides of the leaflets 31 are sutured directly or indirectly to the two arms 32, 33 of the lower part 22b. The lower crown 24 is formed by a substantially tubular portion having a lattice structure of cells 34, 35, 36. The two arms 32, 33 of each wishbone shaped commissural post 22 span a respective sequence of at least three adjacent cells 34, 35, 36. The wishbone extends from outer cells 34, 36 of the sequence without attachment to at least one intermediate cell 35 of the sequence.

The lower, i.e proximal end of the stent is covered by an outer skirt 34 extending axially along about half of the height of the cells 34, 35, 36. On the inner side of the stent 15 there is an inner skirt 35 preferably made of pericardium material sealing the space between two neighbouring arms 32, 33 of a wishbone shaped commissural post 22.

FIG. 2 is a representation of a leaflet 10 according to the present invention. A free edge 10 is configured such as to sealingly engage free edge 10 of at least one further leaflet 31 to form a tightly closing valve. Preferably, the free edge 10 is arcuate, although a straight edge may also be used. The leaflet further includes two lateral edges 11 and a lower edge 12. The lower edge 12 is arcuate, while the lateral edges 11 are linear. The surface framed by the lateral edges 11 and the lower edge 12 is frequently referred to as "belly" of the leaflet 31. Two tabs 30 are arranged on both lateral edges 11 in the area of the free edge 10. The tabs 30 are sized and shaped such as to be insertable into attachment means provided on commissural posts of the stent component of a valve replacement device (see also FIGS. 3 and 4). At least two leaflets 31 are positioned in such a device to form a valve component, but preferably the valve component comprises three leaflets 31.

FIG. 3 shows a detailed view showing the configuration of a stent component 20 having commissural posts 22 in a wishbone shape. The stent component 20 is shown in its collapsed, i.e. crimped state. The upper parts 22a of commissural posts 22 are joined together by stabilization arches 21. Further, these upper parts 22a comprise fixation means for tabs 30 of leaflets 31, here represented by openings 19 and holes 18. The lower part 22b of commissural posts 22 comprises two arms 32, 33. The commissural posts 22 thereby have an overall wishbone shaped configuration. As can be readily seen on this figure, both arms 32, 33 of commissural posts 22 span a sequence of three consecutive cells 34, 35, 36 of the lower crown 24. The arms 32, 33 are thereby connected to the outer cells 34, 36 of the sequence without attachment to the intermediate cell 35 of the sequence. The lower crown 24 further comprises attachment elements 25 in the form of hooks. These attachment elements 25 allow the removable attachment of the valve replacement device 15 to a delivery device.

FIG. 4 shows different configuration of attachment means on the upper part 22a of commissural posts 22. The configuration shown in FIG. 4a corresponds to the configuration of the commissural posts 22 as shown on FIG. 3. An opening 19 in the form of a long hole is arranged in the centre of the upper part 22a. The opening 19 is shaped and sized such as to allow insertion of at least one tab 30. However, the size of the opening 19 is preferably such that two tabs 30 may be inserted. Further, the opening 19 is flanked on both sides by four holes 18. A further hole 18 is arranged on top of the opening 19. The holes 18 are intended to accommodate suture wire used to attach the tabs 30 to the commissural posts 22. An alternative configuration of the opening 19 is shown on FIG. 4b. In this embodiment, the opening 19 is configured as longitudinal slit in the middle of the upper part 22a. Again, the opening 19 is flanked by holes 18. FIG. 4c shows a further embodiment without any holes 18. The opening 19 is shown as longitudinal slit, but may alternatively also be configured as long hole. In this embodiment, tabs 30 are inserted through opening 19, folded back towards the leaflet 31 and sutured thereto. A further alternative embodiment is shown on FIG. 4d. In this embodiment, the attachment means only comprise holes 18. A tab 30 is thereby folded backward onto the leaflet 31 and sutured thereto. A further suture is sewn from the fold of the tab 30 into the openings 18, thereby attaching the tabs 30 to commissural posts 22.

FIG. 5 represents a method of producing a valve replacement device 15 according to the present invention. FIG. 5a shows the first step of the method. A generally rectangular piece of pericardium tissue 2 having an appropriate size is wrapped around a mandrel 1 having an appropriate shape. The mandrel preferably comprises specific shape elements, here exemplarily shown as bulges 4 to be imparted to the inner skirt of the valve replacement device. The pericardium tissue is then sewn together with suture 3 and optionally treaded to impart some shrinkage of the tissue. In the next step, shown on FIG. 5b, at least two but preferably three tabs 31 are arranged around said piece of pericardium tissue 2 on its outside surface. The tabs 31 are thereby arranged such that tabs 30 of neighbouring leaflets 31 are at the same height along the longitudinal axis of the mandrel 1. Further, neighbouring leaflets 31 contact each other at their lateral edges in the area of the tabs 30. The leaflets 31 are then sewn to the pericardium tissue 2 along the lower edge 12 and the lateral edges 11. The tabs 30 remain free. Thereafter, the pericardium tissue 4 is removed from the mandrel 1 and everted (see FIG. 5c). The leaflets 31 are now located on the inside of the cylindrically shaped pericardium tissue 4. Excess material 6 of the pericardium tissue is removed, e.g. by cutting. At least a portion of the pericardium tissue 4 located on the exterior of the leaflets 31 is also removed along suture 7 which connects the pericardium tissue 4 with the leaflets 31. At the area of the tabs, slits 8 are provided in the pericardium tissue 4 which are arranged and sized such as to be able to pass tabs 30 therethrough. At the area of the slits 8, two flaps 9 of the pericardium tissue 4 are left. The tabs 30 are then passed through the slits 8. The now finished valve component 5 includes inner skirt 28 and leaflets 31. With the exception of the area around suture 7, the valve component 5 consists of a single layer of pericardium tissue. In a next step shown on FIG. 5d, the valve component 5 is inserted into the stent component 20. The tabs 30 are inserted through the openings 19 located on the commissural posts 22, folded back toward leaflets 31 and further attached to the commissural posts 22 by suturing. The suture stitches are passed through holes 18. Superfluous material of the tabs 30 is subsequently removed. Then, the flaps 9 are folded over the upper part 22a of the commissural posts 22 to cover the suture of the tabs 30, thus forming a kind of sleeve around the upper part 22a of the commissural posts 22. FIG. 5e shows the finished valve replacement device 15. The valve component 5 is additionally attached to the stent component 20 by means of sutures 13 in the area of the arms 32, 33 of each wishbone shaped commissural posts 22. Further, the inner skirt 28 is attached to the cells of the lower crown 24 by means of sutures 14. The lower crown 24 may additionally be covered on the outside by an outer skirt 29, as shown on the embodiment of FIG. 1.

In some embodiments, the flaps 9 may have an axial extent that is greater, in the inflow and/or outflow direction, than the tabs 30. When the flaps 9 are folded around the commissural post, the flaps 9 may extend axially beyond the edge of the tabs 30, thereby covering and protecting the tabs 30. As can be seen in FIG. 5e, the flaps 9 may extend axially above the level of the leaflets.

FIG. 6 illustrates schematically a modified arrangement of stent component, and a modified arrangement of inner skirt 35 and outer skirt 34. The inflow end or mouth of the stent component has a zig-zag shape defined by cells of a lattice structure including at least one row of lattice cells. The zig-zag shape is defined by alternating free apexes 50 and connected apexes 52. The free apexes 50 define an inflow extremity. The connected apexes 52 communicate with adjacent cells in the row.

The position of the inner skirt 35 is indicated by lines 54 and 56, and extends from the commissural posts and/or leaflets towards the inflow extremity. The line 54 indicates generally the level of the lower edges of the leaflets, although it is to be appreciated that the inner skirt 35 may have commissural portions that extend axially up the commissural posts of the stent component. The position of the outer skirt 34 is indicated by lines 58 and 60 and extends further than the inner skirt 35 towards the inflow extremity.

In the illustrated example, as indicated by the line 56, the inner skirt 35 extends to a level corresponding to (at least some of) the connected apexes 52. The outer skirt 34 extends to a level corresponding to (at least some of) the free apexes 50.

The outer skirt 34 may have a zig-zag shaped edge that matches substantially the zig-zag shape of the inflow edge.

The inner skirt 35 extends further than the outer skirt 34 in the opposite direction towards the outflow end (and/or extremity) of the stent. The inner and outer skirts may partly overlap each other in the axial direction. The degree of axial overlap may, for example, be at least 1 mm, or at least 2 mm, or at least 3 mm, or at least 4 mm, or at least 5 mm, or at least 6 mm, or at least 7 mm, or at least 8 mm. Additionally or alternatively, the degree of skirt overlap in the axial direction may, for example, be less than 10 mm, or less than 9 mm, or less than 8 mm, or less than 7 mm, or less than 6 mm, or less than 5 mm, or less than 4 mm. For example, the degree of skirt overlap in the axial direction may be about 4-6 mm.

As can be seen in FIG. 6, at least some of the cells have an exposed free apex 50a that extends beyond the free apexes 50 of adjacent cells in the row, and is not covered by the outer skirt 34. The exposed free apexes 50a provide attachment elements 25 for engaging a stent holder of a delivery device.

Also as can be seen at the circle A in FIG. 6, and the corresponding area in FIG. 3, suture bores may be provided along each side of the opening in the commissural post, and at only one axial end of the stem. Such an arrangement can enable the size of the stem of the commissural post to be reduced compared to an arrangement in which suture bores might be provided at both axial opposite ends.

FIG. 7 illustrates schematically a delivery device 62, e.g. delivery catheter, for inserting the valve replacement device at the heart. The catheter may be advanced over a guidewire (shown by the broken line). The catheter comprises a distal portion 64 for insertion into the anatomy and having an accommodation region for accommodating the valve replacement device in its compressed state. A stent holder (described below) is provided at the accommodation region for restraining the valve replacement device against axial movement until the stent component expands to its functional state, whereupon the stent component detaches from the stent holder. The distal portion 64 may also include a sheath arrangement for constraining the stent-component in its compressed state for delivery, the sheath arrangement being operable to unsheath the stent component to allow the stent-component to expand to its functional state. The delivery catheter 62 further comprises a stem portion 66, which is optionally flexible, extending towards a proximal portion 68 having a control handle.

Different examples of attachment elements 25 are envisaged. Generally, each attachment element 25 may be defined by an apex joining first and second struts that extend from an end of the stent component. The struts may be members defining a lattice or skeletal stent structure of the stent-valve 10. In the case of a lattice, the cell associated with the struts may project axially beyond neighbouring cells of the lattice.

In FIG. 3, the struts may extend generally linearly to meet at an apex defining a generally straight-sided U-shape in the compressed state (illustrated in FIG. 3), and expanding to a V-shape when the stent component expands to its functional state. In FIG. 6, the apex is slightly different by having a generally rounded or horseshoe U-shape when in the compressed state (illustrated in FIG. 6), and expanding to a generally non-horseshoe shape, e.g. to a straight sided U-shape (FIG. 9), when the stent component expands to its functional state.

Referring to FIG. 8, the stent holder 78 may generally comprise a plurality of projections 84 and/or interstices 86 for accommodating the attachment elements 25 of FIG. 3 and/or FIG. 6. The edge 90 of each interstice 86 may optionally be rounded or chamfered. The projections 84 may be configured for fitting within the interior of the apex of each attachment element 25, when the stent component is in its collapsed state. The engagement between the projection 84 and the attachment element restrains the attachment element (and hence the stent-valve 10) against axial movement, at least in an axial direction away from the stent holder 24, and optionally in both axial directions.

In the case of a self-expanding stent component, the attachment elements 25 may disengage when the portion of the stent component from which the attachment elements 25 extend, is uncovered by the sheathing arrangement of the delivery catheter. Upon expansion of the stent component, the struts move apart to open the U- or V-shape of the attachment element apex. As the apex opens, this enlarges the interior of the attachment element 25 to facilitate disengagement between the projection 84 and the attachment element 25. The chamfered edge 90 of the interstice 86 also acts as a ramp surface to "lift" radially the struts out of the clearance 88 as the struts expand circumferentially and bear against the edge 90. In case the attachment elements 25 may stick accidentally within the interstice 86, the attachment elements 25 may be freed by slight rotation and/or axial displacement of the catheter, to promote further riding against the edge 90.

In the specific example of FIGS. 6, 8 and 9, the projections 84 are fingers or pins, suitable for fitting within the interior of the horseshoe shape of the attachment element. The projections may be generally radially projecting, or may be inclined at an angle away from the stent component, for example, at an angle of up to about 10 degrees (e.g. about 5 degrees). In a collapsed state of the stent component (FIGS. 6 and 8), the struts may lie closely adjacent each other at the attachment element 25, such that the arc of the U-shape portion 25 extends around a first angle more than 180 degrees to define a closed or near closed eyelet having an aperture larger than the spacing of the struts, to accommodate the pin 84. The eyelet aperture and space between the struts may together define a keyhole type shape. Alternatively, the struts may bear against each other at the attachment element 25 to close the eyelet. Either arrangement can restrain the attachment element 25 in both axial directions, merely by engagement between the attachment element 25 and the projection 84. This may be advantageous by enabling a larger chamfer surface to be used at the edge 90 of the interstice 86 and/or at the end face 92 of the stent-holder. A chamfered end face 92 may be desirable to facilitate withdrawal of the stent holder 78 through the valve replacement device once implanted. The arrangement also allows the struts of the attachment element to be compressed close together, such that the provision of the attachment element does not impede compressing the stent component to a desirably small size.

Optionally, the interstice 86 is closed at one axial end, to provide additional protection against the attachment element 25 displacing axially in a direction that would force the projection 84 into the space between the struts.

Referring to FIG. 9, in the expanded (or non-collapsed) functional state of the stent component, the struts may move apart, and the arc of the U-shape apex may extend around a second angle that is less than the first angle, to at least partly open the eyelet. The second angle may be about 180 degrees or less. In a similar manner to that described above, opening of the apex may facilitate disengagement from the projection 84. The chamfered edge 90 of the interstice 86 also acts as a ramp surface to "lift" radially the struts out of the clearance 88 as the struts 70 and 72 expand circumferentially and bear against the edge 90.

It is emphasized that the foregoing description is merely illustrative of non-limiting preferred forms of the invention. Many modifications and equivalents may be used within the scope of the invention.

The invention claimed is:

1. A valve replacement device for transcatheter implantation, comprising:
   a stent component having an inflow extremity and an outflow extremity, the stent component being radially compressible to a compressed state for delivery to a site of implantation and radially expandable to a functional state, wherein the stent component further comprises an intermediate section between the inflow extremity and the outflow extremity, the intermediate section comprising at least two commissural posts;
   valve leaflets mounted at least partly within the stent component;
   an inner skirt attached to the valve leaflets, the inner skirt extending at least partly within the stent component towards the inflow extremity; and
   an outer skirt extending at least partly outside the stent component, the outer skirt extending further than the inner skirt towards the inflow extremity;
   wherein the leaflets are attached to the inner skirt, the inner skirt having commissural portions spaced by scallop-shaped clearances, each clearance spanned by a leaflet, and wherein each commissural portion of the inner skirt comprises at least one flap that is folded at least partly around a respective commissural post.

2. The device of claim 1, wherein the inner skirt and the outer skirt partly overlap in an axial direction.

3. The device of claim 1, wherein the inner skirt extends further than the outer skirt towards the outlet extremity of the stent component.

4. The device of claim 2, wherein the inner skirt extends further than the outer skirt towards the outlet extremity of the stent component.

5. The device of claim 1, wherein a mouth of the stent component has a zig-zag shape defined by a lattice structure of at least one row of cells, the zig-zag shape being defined by an alternating sequence of free apexes at the inflow extremity and connected apexes connecting to adjacent cells, the inner skirt extending only to a level corresponding to at least some of the connected apexes, and the outer skirt extending to a level corresponding to at least some of the free apexes.

6. The device of claim 1, wherein a row of cells at a mouth of the stent component includes at least first and second cells having an exposed free apex that extends beyond free apexes of adjacent cells in the row and is not covered by the outer skirt, the exposed free apexes providing attachment elements for engaging a stent-holder of a delivery device for delivering the valve replacement device to a site of implantation.

7. The valve replacement device of claim 1, wherein the stent component comprises at least one attachment element for cooperating with a stent-holder of a delivery catheter, wherein the attachment element comprises a U-shape portion joining two stent struts, and wherein, in the compressed state of the stent component, the struts lie adjacent each other at the attachment element, such that an arc of the U-shape portion extends around a first angle more than 180 degrees to define a closed or near closed eyelet having an aperture larger than a spacing of the struts, and wherein, in the functional state of the stent component, the struts displace apart, and the arc of the U-shape portion extends around a second angle that is less than the first angle, to at least partly open the eyelet.

8. The device of claim 7, wherein in the compressed state, the U-shape of the attachment element is a horseshoe U-shape.

9. The device of claim 7, wherein in the functional state, the U-shape of the attachment element is not a horseshoe U-shape.

10. A valve replacement device for transcatheter implantation, comprising:
a stent component comprising a first end, a second end and at least one intermediate section arranged between the first end and the second end, the stent component being radially compressible to a compressed state for delivery to a site of implantation and radially expandable to a functional state, the intermediate section comprising at least two commissural posts each in a shape of a wishbone including a stem communicating with adjacent stent structure and two legs communicating with adjacent stent structure, and
at least two valve leaflets supported by the stent component, each valve leaflet including at least two tabs directly attached to the commissural posts, wherein the at least two valve leaflets are attached to an inner skirt, the inner skirt extending at least partly within the stent component;
wherein the leaflets are attached to the inner skirt, the inner skirt having commissural portions spaced by scallop-shaped clearances, each clearance spanned by a leaflet, and wherein each commissural portion of the inner skirt comprises at least one flap that is folded at least partly around a respective commissural post.

11. The device of claim 10, wherein the stent component comprises a lattice structure having at least one row of cells arranged between the intermediate section and the second end, the wishbone shape of each commissural post spanning a respective sequence of at least three adjacent cells such that the wishbone extends from outer cells of the sequence without attachment to at least one intermediate cell of the sequence.

12. The device of claim 10, wherein the tabs of the leaflets are attached to the stem of the wishbone shaped commissural posts.

13. The device of claim 10, wherein the legs of the wishbone shaped commissural posts are shaped such as to match lateral edges of the leaflets.

14. The device of claim 10, wherein the at least two commissural posts are connected together by at least two stabilization arches arranged between the first end and the intermediate section.

15. A valve replacement device for transcatheter implantation, comprising:
a stent component comprising a first end, a second end and at least one intermediate section arranged between the first end, and the second end, the stent component being radially compressible to a compressed state for delivery to a site of implantation and expandable to a functional state, the intermediate section comprising at least two commissural posts;
an inner skirt extending at least partly within an interior of the stent component; and
at least two valve leaflets each including at least two tabs, the tabs projecting through slits in the inner skirt and attached directly to the commissural posts;
wherein the leaflets are attached to the inner skirt, the inner skirt having commissural portions spaced by scallop-shaped clearances, each clearance spanned by a leaflet, and wherein each commissural portion of the inner skirt comprises at least one flap that is folded at least partly around a respective commissural post.

16. The device of claim 15, wherein tabs of two adjacent leaflets meet and project through the same slit in the inner skirt, and are attached directly to the same commissural post.

17. The device of claim 15, wherein each tab is attached directly to the commissural post by passing through a slot in the commissural post and/or being sutured to the commissural post.

18. The device of claim 15, wherein each commissural portion of the inner skirt comprises two flaps that are folded at least partly around a respective commissural post.

19. The device of claim 15 wherein the at least one flap covers a portion of the tab that is attached to the commissural post.

20. The device of claim 15, wherein the at least one flap extends axially beyond an edge of the tab that is attached to the commissural post.

* * * * *